(12) United States Patent
Luotio

(10) Patent No.: US 6,250,924 B1
(45) Date of Patent: Jun. 26, 2001

(54) DENTAL IMPLANT SYSTEM AND A METHOD FOR ITS MANUFACTURE

(76) Inventor: Kari Luotio, Kumputie 3, Fin-47200, Elimaki (FI)

( * ) Notice: Subject to any disclaimer, the term of this patent is extended or adjusted under 35 U.S.C. 154(b) by 0 days.

(21) Appl. No.: 09/269,362

(22) PCT Filed: Apr. 17, 1998

(86) PCT No.: PCT/FI98/00342

§ 371 Date: Mar. 23, 1999

§ 102(e) Date: Mar. 23, 1999

(87) PCT Pub. No.: WO98/47441

PCT Pub. Date: Oct. 29, 1998

(30) Foreign Application Priority Data

Apr. 17, 1997 (FI) ........................................................ 971622

(51) Int. Cl.$^7$ ................................................................ A61C 8/00
(52) U.S. Cl. ................................................................ 433/173
(58) Field of Search .................................... 433/172, 173, 433/177

(56) References Cited

U.S. PATENT DOCUMENTS

| | | | |
|---|---|---|---|
| 2,644,231 | * | 7/1953 | Brennan ................................. 433/173 |
| 4,439,152 | * | 3/1984 | Small ..................................... 433/173 |
| 4,516,937 | * | 5/1985 | Bosker .................................. 433/173 |
| 4,784,608 | * | 11/1988 | Mays ..................................... 433/173 |
| 4,832,601 | * | 5/1989 | Linden ................................... 433/173 |
| 5,052,928 | * | 10/1991 | Andersson ........................... 433/172 |
| 5,064,374 | * | 11/1991 | Lundgren ............................. 433/173 |
| 5,219,286 | * | 6/1993 | Hader .................................... 433/172 |
| 5,427,906 | * | 6/1995 | Hansen ................................. 433/173 |
| 5,460,526 | * | 10/1995 | Bosker .................................. 433/173 |
| 5,630,717 | * | 5/1997 | Zuest et al. .......................... 433/172 |

* cited by examiner

*Primary Examiner*—Ralph A. Lewis
(74) *Attorney, Agent, or Firm*—Fay, Sharpe, Fagan, Minnich & McKee, LLP

(57) ABSTRACT

The invention relates to a dental implant system for attaching a prosthesis to a patient's gum. The system includes implanted screws which are lined up with substantially similarly sized support extensions. The support extensions are connected using a screw-secured bar to make a support component. The support component is fixedly secured to the implant screws through use of adjusting screws. These adjusting screws also help to align the support component and the implant screws very precisely with respect to each other. In a method of manufacture for the dental implant system, precisely fitting screws are attached to working model screws that correspond to implant screws in the patient's gum. Then telescopic collars are set on top of the precisely fitting screws and fit flush with the head of the working model screws. Next, the collars are attached to each other using a transverse bar in an area just above the gum locking the collars into position. Finally, the detachable collars and the bar are used to make a casting mold for the support component containing the bar, which penetrates the gums and is supported with flush fitting in the upper surfaces of the implant screws.

22 Claims, 3 Drawing Sheets

DENTAL IMPLANT SYSTEM AND A METHOD FOR ITS MANUFACTURE

BACKGROUND OF THE INVENTION

The present invention relates to a dental implant system and a method for its manufacture. More precisely, the invention concerns a system, by means of which a highly permanent and precise removable prosthesis can be created, especially for a patient's mandible.

Implant treatment, as such, has been known for decades. In general, an implant refers to a screw or cylinder permanently set in a hole drilled in the patient's mandible or maxilla, which can support various prosthetic structures. The screw or cylinder is nearly always made from titanium.

When it is wished to construct a removable full mandible prosthesis on implants, it has usually been carried out until now by first of all setting the implant screws in place in the mandible. Once the screws have become firmly osteointegrated (i.e. ossified) in the mandible, extensions penetrating the gum (mucous membrane inserts) are screwed into them. Attachment is by means of the conical upper surface of the implant fitting a conical counter surface in the extension. However, implants are also used, in which there is a shoulder joint surface and a corresponding shoulder joint surface in the extension. Implants are also used, which themselves penetrate the gum (i.e. gingiva). A bar is constructed on the part above the gum and the prosthesis is attached by suitable means, such as a snap-fastener (riders) or attachments.

This is only an approximate description of the procedure, because in practice modern systems contain tens, if not hundreds of different parts. Though these are naturally intended to create an optimal solution for each case, the large number of parts is a nuisance to both the manufacture and the dentist.

Another serious drawback of the known structures is the difficulty of creating a good fit between the adjustment surfaces described above. In itself, it is easy to create as good fit using conical or shoulder connection surfaces, but if the same assembly contains several joints formed by conical connection surfaces, adjustment becomes extremely difficult. Conical connection surfaces are very difficult, as it is awkward to create a good fit in more than one joint between a screw and an extension and then between the extension and the bar. Thus, in known systems, a great deal of attention must be paid to the parallelism of the implants.

Another problem with conical fitting joints is that because certain movement tolerances are used relative to the parts to be joined, known systems often have connections in which steps are formed in the connection surface. Such steps form areas in the prosthetic system that irritate tissue and induce bacterial growth.

The present invention contemplates a new and improved apparatus and method which overcomes the above-referenced problems and others.

SUMMARY OF THE INVENTION

In accordance with the present invention there is provided a dental implant system, and a method of its manufacture. The implant system includes at least two support points for attaching a mandible prosthesis. The implant system also includes implant screws attached to a patient's mandible and a screw-secured bar supported by them for securing and supporting the mandible prosthesis. The bar is part of a support component that is directly supported, without intermediate pieces and with flush fitting by virtue of support extensions parallel to the implant screws and uniform with the support component, on the implant screws attached to the mandible by means of a joint beneath a surface of the patient's gum.

In accordance with another embodiment of the current invention, a method of manufacture for the dental implant system includes the steps of attaching precisely fitting screws to working model screws that correspond to implant screws in the patient's gum. Then telescopic collars are set on top of the precisely fitting screws and fit flush with the head of the working model screws. Next, the collars are attached to each other using a transverse bar in an area just above the gum locking the collars into position. Finally, the detachable collars and the bar are used to make a casting mold for the support component containing the bar, which penetrates the gums and is supported with flush fitting in the upper surfaces of the implant screws.

One advantage of the present invention is that the provision of a dental system, and a method for its manufacture, which results in a precise fitting between the parts of the implant system.

Another advantage of the present invention is that the dental system ensures installation in relation to the occlusion lines in a way that guarantees maximum durability.

Other advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating the preferred embodiments of the invention and are not to be construed as limiting same and wherein.

DETAILED DESCRIPTION OF THE PREFERRED EMBODIMENT

Figure 1:
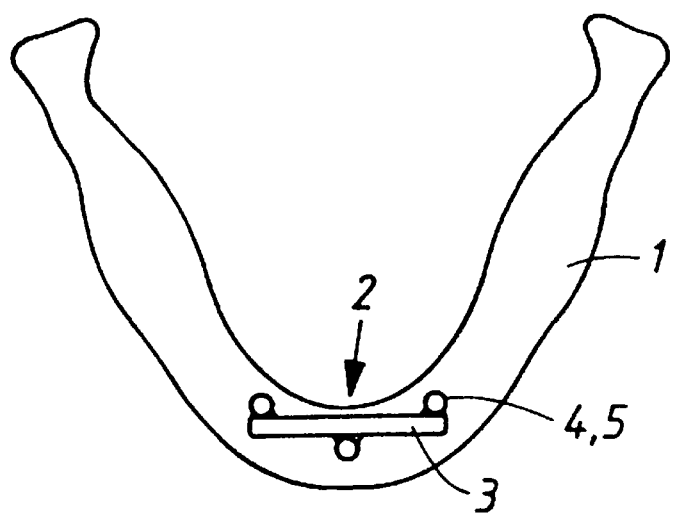
FIG. 1 shows a diagrammatic general horizontal view of a bar located in the mandible supported on implants, on which in turn the mandible prosthesis is set.

Thus, FIG. 1 shows a rough diagram of a patient's mandible, seen from directly above, in a situation in which the ready system (without the actual prostheses) is attached to the patient's mandible 1. Thus, the diagram shows, in the area above the patient's gum, the metal support 2, which consists of a bar component 3, to which the actual prosthesis is attached, for example, by means of riders ("snap-fasteners"), and a extension 4, which becomes a vertical component and which is penetrated by attachment screw 5. Screw 5 attaches the structure to the implants, which have been attached to the mandible in a previous stage.

Figure 2:
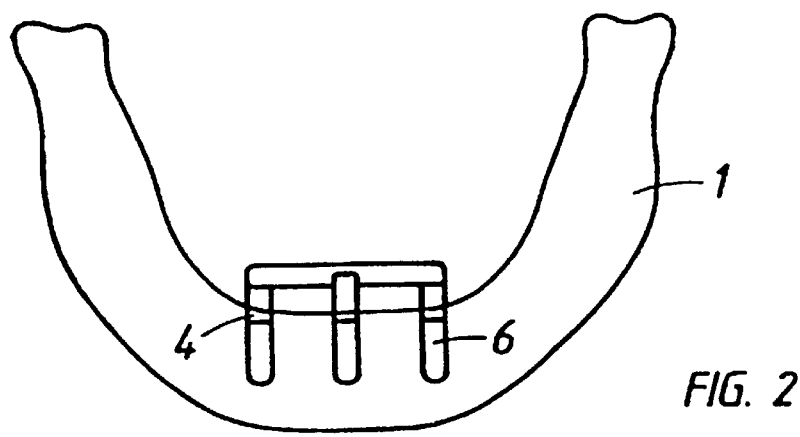
FIG. 2 also shows a diagram of a front (i.e. frontal) view of an implant system manufactured according to the invention, also showing the outline of the mandible.
Figure 3:
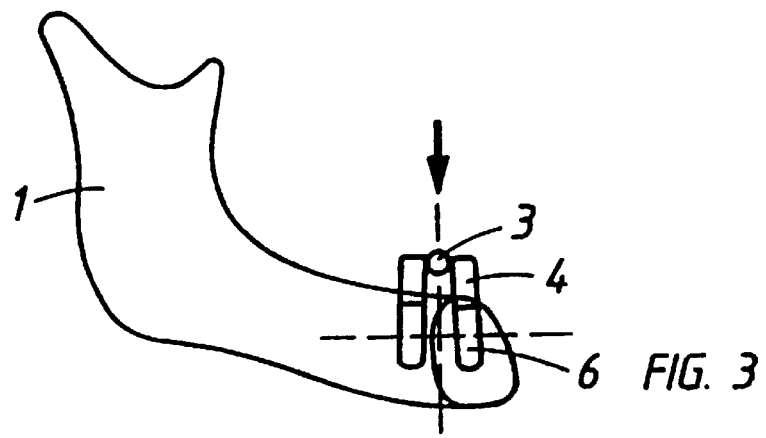
FIG. 3 also shows a diagram of a side (i.e. sagital) view of an implant system manufactured according to the invention, also showing the outline of the mandible.

FIG. 2 also shows a rough diagram of the structure in FIG. 1 in a front view and FIG. 3 in a side view. Mandible 1 is articulated to the base of the skull by two condyles. Holes are drilled in the mandible, in which the actual implants 6, made from specially treated titanium, are set. The implants 6 are allowed to embed in the bone tissue for a suitable period of time.

A metal support section 2, which includes the bar 3 and the extensions 4 which penetrate the gum, is supported by the implants 6 and fitted tightly to them. The prosthesis is attached to bar 3 and is supported for part of its length by the mucous membrane of the patient's mandible. It should be noted that if the attachment bar, viewed from above and from the side, is set between the implants in parallel with the line between the joints, and if the masticatory force (arrow in FIG. 3), when viewed from the side, is directed through the centre point of the implantation, as is shown in FIG. 3 by horizontal and vertical broken lines, the structure will be affected by the minimum possible detrimental stresses.

Figure 4:
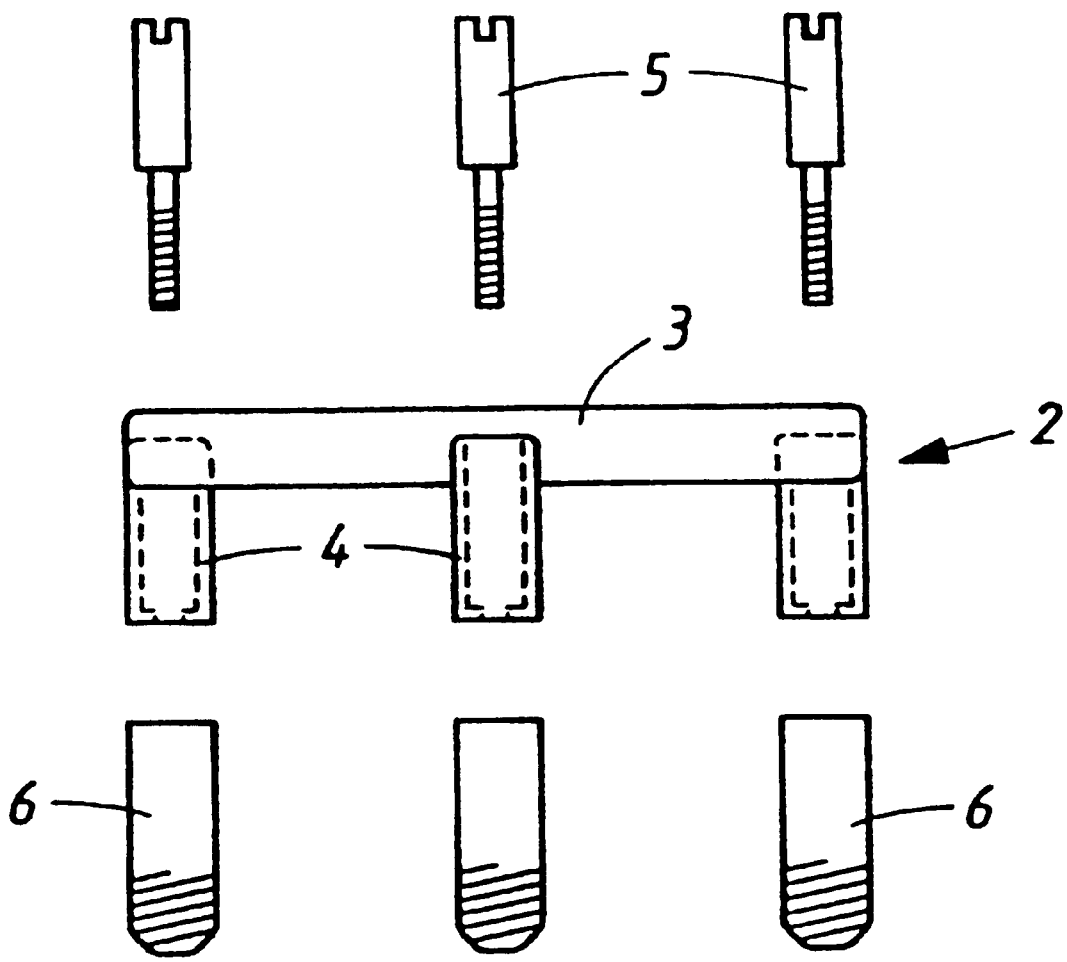
FIG. 4 shows the parts of the system according to the invention separated from each other, in a position in which they can be attached to each other.

FIG. 4 shows the components of the implant system according to the invention ready for installation, seen diagrammatically from directly in front. At its simplest, the system comprises three different components; firstly the implant screws 6, secondly the support component 2, which is supported by and attached to them and which includes the extensions 4 and bar 3 for attaching the prosthesis, and thirdly the precisely adjustable screw 5, which is intended on the one hand to adjust parts 2 and 6 very precisely to each other, and on the other hand to secure the aforesaid components to each other.

There are two points that should be noted about the above structure. The first is that the connection of the implant screws 6 and component 2 to each other is by means of a flush fit and not a conical or shoulder connection. The second is that component 2 is supported by means of the extensions 4 directly on the implant screws beneath the surface of the gum at the level of the bone. Thus a system according to the invention has only a few components, compared to the multitude of parts in previous systems.

The system according to the invention would not be possible, unless there was a method permitting the system described to be made in a manner allowing the parts to be fitted to each other with extreme precision. Next, a method will be described, by means of which the aforementioned extremely advantageous structure can be created.

In practice there may be a certain, quite large angle between the implant screws in the mandible. In particular, it may be advantageous to set the implant screws in a certain fan-shaped way. In that case, for example, the implant screws which are in front will be slightly sloping to the front, while the rear screws will be slightly sloping to the back.

In this way an extremely advantageous situation is achieved in the ability to bear masticatory forces. The achievement of the above described fan-shaped installation, or an installation which in any case differs from a parallel installation system, has caused great difficulties in the application of structures on the bone level that are supported by implants. Now, the installation of implant screws or cylinders can be performed so that the physical properties of the mandible, especially the quantity of bone, can be taken into account to achieve the optimal end result.

Figure 5:
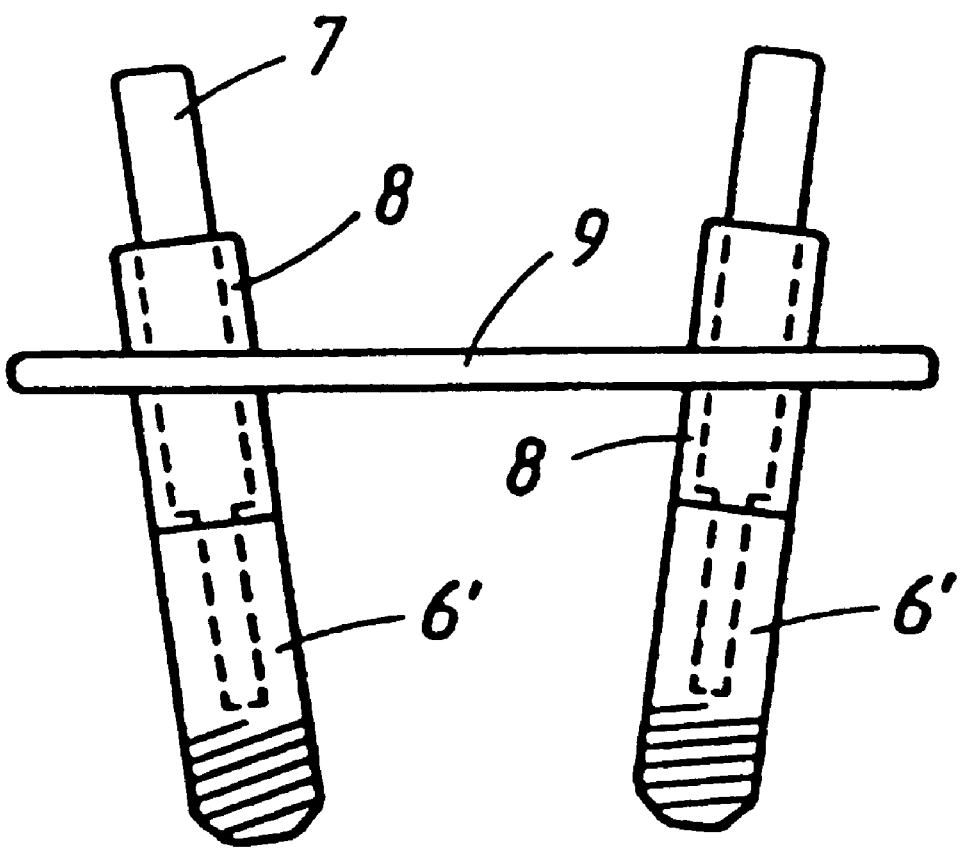
FIG. 5 shows the stages in the method that ensures the compatibility of the implants and the related structures.

FIG. 5 shows diagrammatically a method by which it is possible to guarantee the above-described optimal conditions in all situations. After a healing period the position of the implants is duplicated using standard methods known in dentistry, and a working model is produced in which precisely fitted screws 7 are screwed into the screws 6' of the working model corresponding to the implants, of which, although only two are shown in FIG. 5, there may be many. Extremely precisely fitted collars 8 are also slipped over the screws 7 so as to be tightly fitted not only against screws 7 but also against the upper surface of screws 6' which correspond to the position of the implants. The whole assembly is thus completely linear. The relationship between screws 7 and collars 8 is therefore telescopic-like. The collars 8 are supported by screws 7, but nevertheless can freely slide up and down them. Alternatively, the collars 8 can be advantageously equipped with a shoulder structure on the end facing the screws 6', with the help of which the screws 7 tighten the collars against the screws 6'.

Transverse bar 9, which locks collars 8 to each other in precisely the position in which they are at the time, is now attached in a suitable manner to the collars 8 in the area above the gum in the working model. Obviously, if there are, for example, four screws corresponding to implants, the transverse bar 9 is attached to every collar 8 of the securing screws 7. It is advantageous to use a plastic material for the collars and bar, so that it is easy to attach the collars 8 and the bar 9 to each other in the desired way. It is then also possible, for example, to use heat to form bar 9 to the desired shape, which then acts as a model for casting.

Once bar 9 has been attached to the collars 8, and the mutual locations and orientations of the components has been thus ensured, the screws 7 are unscrewed from the working model's screws corresponding to the implants, whence the total structure formed by 8 and 9 can be lifted out and used to manufacture a casting mould, using routine methods of dentistry; i.e. a mould is made on top of components 8 and 9, from which the plastic material is removed by heating, and the resulting cavity is used as a casting mould. It is obvious that the cast piece must be suitably finished after casting.

The final result is a cast piece consisting of support component 2, which fits perfectly the upper surface of the implant screws in the mandible, in relation to both the direction of the surfaces and the dimensions of the parts. This support component 2 is then screwed to the implant screws 6 by means of screws 5 and the mandible prosthesis is attached to bar 3.

The components according to the invention are always made from biocompatible metals and alloys approved by dentistry. The surface of implant screw 6 is of specially treated titanium. The materials used for support component 2 can be titanium or gold or chrome-cobalt alloys.

It is clear that the invention can be adapted in many ways, while nevertheless remaining within the scope of the inventive idea and the accompanying claims. Thus, for example, after the installation of the implant screws, so-called primary healing screws can be used to create a beneficial effect on the edge of the bone. Similarly, secondary healing screws can be used to create a similar effect on the gum.

It is also clear that during the operations needed for making the structures referred to above, normal changes in dimensions occur. The experts in this field, however, have learned to handle this kind of changes very well and routine procedures are also used when adapting this invention into practice.

Although the foregoing describes, as an embodiment of the invention, only a support for the mandible prosthesis, it is self-evident that the invention can be applied equally well to any such use whatsoever in which at least two implant screws are employed. For example, various bridge constructions can be made from this kind of support.

The invention has been described with reference to the preferred embodiment. Obviously, modifications and alterations will occur to others upon reading and understanding the proceeding detailed description. It is intended that the invention be construed as including all such modifications and alterations insofar as they come within the scope of the appended claims or the equivalents thereof.

What is claimed is:

1. A dental implant system, which includes at least two support points, for attaching an oral prosthesis, the system comprising:

at least two implant screws adapted to be attached to a patient's jaw, said at least two implant screws each having a single, relatively planar implant end surface; and a support member for securing and supporting the prosthesis, said support member comprising integral support extensions protruding therefrom each extension having a single, relatively planar distal end surface in direct abutting contact with a respective one of said implant end surfaces, wherein the distal end surfaces and the implant end surfaces are parallel to one another and abutting contact only occurs between them without intermediate pieces therebetween, said support extensions being each oriented in substantially parallel relation to one of said at least two implant screws.

2. The system according to claim 1, wherein outer dimensions of the support extensions are substantially a same size as outer dimensions of the implant screws.

3. The system according to claim 1, wherein a line of said support member is oriented along a line between a pair of mandible joints.

4. The system according to claim 1, wherein the support member, which attaches between the implant screws, when viewed from above and in front, is set parallel to a line between a patient's mandibular condyles and, when viewed from a side, is set in such a way that a masticatory force acts through a center point of the dental implant system.

5. The system according to claim 1, further comprising at least two fine adjusting screws, a respective one being inserted through an aperture disposed in each of the support extensions into each of the implant screws to secure the support member to the implant screws and precisely align the support member and the implant screws.

6. The system according to claim 1, further comprising at least two fine adjusting screw, a respective one being inserted through an aperture disposed in each of the support extensions into each of the implant screws such that the adjusting screw adjusts a fit between the support member and the implant screws until the support member and the implant screws are precisely aligned.

7. The system of claim 1 wherein three implant screws cooperate with three support extensions of said support member, wherein one of said implant screws and said support extensions is located in a different plane from a plane of the other two implant screws and support extensions.

8. The system according to claim 1 wherein a first of the support extensions is disposed on a first side of the support member, and a second of the support extensions is disposed on a second and opposing side of the support member.

9. A method for manufacturing a screw-secured bar of a dental implant system for attaching a prosthesis to a mandible, the dental implant system including attachment of implant screws to the mandible and using them to support the screw-secured bar for attachment and support of the prosthesis including the steps of:

manufacturing a working model having working model screws that correspond to implant screws preset in a patient's mandible;

threading precisely fitting first screws into the working model screws;

setting precisely fitting telescopic collars on top of the first screws that also fit flush with a head of the working model screws;

attaching the telescopic collars to each other by means of a single transverse bar in an area representative of an area above a patient's gum, which completely locks the telescopic collars into position; and, manufacturing a screw-secured bar from a casting mold, wherein a combination of the telescopic collars and the transverse bar is used to make the casting mold for the screw-secured bar, which penetrates the patient's gums and is supported with flush fitting on upper surfaces of the implant screws.

10. The method according to claim 9, wherein the telescopic collars and the transverse bar are manufactured from a plastic material, which is removable by heating from the casting mold.

11. The method according to claim 9 wherein the step of attaching the telescopic collars to each other by means of a transverse bar includes the step of:

positioning one of the telescopic collars on a first side of the transverse bar and positioning another one of the telescopic collars on a second and opposing side of the transverse bar.

12. A dental implant system for attachment to a patient's mandible, the system comprising:

a lower structure including at least two implants capable of being placed in the mandible, each of the implants having a threaded opening;

an integral upper structure including at least two connecting pieces extending from a bar, said at least two connecting pieces having a substantially identical outside diameter to an outside diameter of the at least two implants, wherein one of said at least two connecting pieces is disposed on a front side of a longitudinal axis of said bar and another of said at least two connecting pieces of disposed on a rear side thereof, and an opening on each end of said at least two connecting pieces having substantially a same diameter as a threaded opening;

at least two screws; and, wherein a first one of said at least two screws is inserted into a first one of the at least two connecting pieces and a second one of the said at least two screws is inserted into a second one of the at least two connecting pieces, wherein each screw extends into a respective threaded opening of said at least two implants.

13. The system in claim 12, wherein the at least two screws are fine-adjustment screws which are used to secure the upper and lower structures.

14. The system in claim 13, wherein the fine-adjustment screws are used to precisely align the upper and lower structures relative to each other.

15. The system in claim 12, wherein the at least two implants are capable of being positioned in the mandible parallel to one another and substantially normal to the bar, which is oriented along a line from a first to a second joint of the mandible, and the at least two connecting pieces extend substantially normal to the bar so that they rest on the surface of the implants.

16. The system in claim 12, wherein the at least two implants are capable of being positioned in the mandible at an angle relative to the bar, wherein the bar is oriented along a line from a first to a second joint of the mandible, and the at least two connecting pieces extend from the bar at an angle which is substantially the same as an angle of the implants so that they rest on the surface of the implant.

17. The system of claim 12, wherein three implants, connecting pieces, and screw are provided and wherein one of said implants and connecting pieces is located in a different plane from a plane of the other two implants and connecting pieces.

18. The system of claim 12 wherein said at least two connection pieces rest substantially flat on the at least two implants to completely cover a surface of the at least two implants.

19. The system of claim 12 wherein said at least two screws each comprise a head and a threaded shaft, wherein said head has a length which is approximately the same as a length of said threaded shaft.

20. The system of claim 19 wherein said at least two connection pieces each include an elongated socket for accommodating a head of a respective one of said least screws.

21. A dental implant system for attaching a prosthesis, the system comprising:
   two implant screws each having a single, relatively planar implant end surface adapted to be attached to a jaw; and
   an integral bar member for attachment of the prosthesis, the bar member comprising two support extensions protruding therefrom, wherein each of the support extensions directly and abuttingly contacts a respective one each of the plurality of implant screws with a flush fit only along a single plane of contact.

22. The system according to claim 21 wherein the system comprises three implant screws and the integral bar member comprises three support extensions protruding therefrom, one support extension disposed on a front side of the bar member and two support extensions disposed on a rear side of the bar member, wherein the two support extensions disposed on the rear side of the bar member are located near opposing ends of the bar member.

* * * * *